United States Patent [19]
Datta et al.

[11] Patent Number: 5,547,870
[45] Date of Patent: Aug. 20, 1996

[54] OXALATE DECARBOXYLATE

[75] Inventors: Asis Datta; Anuradha Mehta; K. Natarajan, all of New Delhi, Ind.

[73] Assignee: Zeneca Limited, London, United Kingdom

[21] Appl. No.: 324,533

[22] Filed: Oct. 18, 1994

Related U.S. Application Data

[63] Continuation of Ser. No. 985,695, Nov. 30, 1992, abandoned.

[51] Int. Cl.$^6$ .............................. C12N 5/04; C12N 9/88; C12N 15/60; C12N 15/82
[52] U.S. Cl. .................. 435/240.4; 435/232; 435/320.1; 536/23.2
[58] Field of Search ............................ 435/172.3, 320.1, 435/240.4, 232; 536/23.2; 935/30

[56] References Cited

U.S. PATENT DOCUMENTS

| | | | |
|---|---|---|---|
| 4,652,452 | 3/1987 | Hiatt et al. | 435/93 |
| 4,956,282 | 9/1990 | Goodman et al. | 435/69.51 |
| 5,169,770 | 12/1992 | Chee | 435/172.3 |

FOREIGN PATENT DOCUMENTS

| | | |
|---|---|---|
| 8808450 | 11/1988 | WIPO . |
| 9215685 | 9/1992 | WIPO . |

OTHER PUBLICATIONS

Chiriboga, "Purification and properties of oxalic acid oxidase", Arch. Biochem. Biophys., vol. 116, 516–523 1966.
Sugiura et al, "Purification and properties of oxalate oxidase from barley seedlings", Chem. Phar. Bull., vol. 27, 2003–2007, 1979.
Grzelczak et al, "Synthesis and turnover of proteins and mRNA in germinating wheat embryos", Can. J. Biochem., vol. 60, 389–397, 1982.
Pietta et al, "Improved purification protocol for oxalate oxidase from barley roots", Prep. Biochem., vol. 12, 341–353, 1982.
Grzelczak et al, "The growth-related 28-kilodalton protein in germinating wheat", Can. J. Biochem., Cell. Biol., vol. 61, 1233–1243, 1983.
Young et al, "Efficient isolation of genes by using antibody probes", Proc. Natl. Acad. Sci., USA, vol. 80, 1194–1198, 1983.
Grzelczak et al, "Signal resistance of a soluble protein to enzymic proteolysis", Can. J. Biochem., Cell. Biol., vol. 62, 1351–1353 (1984).
Grzelczak et al, "Germin. Compartmentation of the protein, its translatable mRNA, and its biosynthesis among roots, stems, and leaves of wheat seedlings", Can. J. Biochem., Cell. Biol., vol. 63, 1003–1013, 1985.
Koyama et al, "Purification and characterization of oxalate oxidase from Pseudomonas sp. OX–53", Agric. Biol. Chem., vol. 52, 743–748, 1988.
Magro et al, "Enzymatic oxalate decarboxylation in isolates of *Sclerotinia sclerotiorum*", FEMS Microbiol. Lett., vol. 49, 49–52, 1988.
Dratewka-Kos et al, "Polypeptide structure of germin as deduced from cDNA sequencing", J. Biol. Chem., vol. 264 4896–4900, 1989.
Ahokas, "Transfection of germinating barley seed electrophoretically with exogenous DNA", Appl. Genet. vol. 77, 469–472, 1989.
Linthorst et al, "Constitutive expression of PR–proteins PR–1, GRP and PR–S in tobacco has no effect on virus resistance", The Plant Cell, vol. 1, 285–291, 1989.
Schmitt et al, "Barley seedling oxalate oxidase purification and properties", Supplement to Plant Physiology, vol. 96, 1991.
Mehta, A. et al. J. Biol. Chem. 266:23548–23553 (1991).
Horsch, R. B. et al. Science 277:1229–1231 (1985).
Sambrook, J. et al. *Molecular Cloning: A Laboratory Manual*, 2nd edition (1989), pp. 12.2–12.15.
Kimmel, A. R., *Methods in Enzymology*, vol. 152, pp. 393–399 (1987.).
Shimazono, H. *J. Biol. Chem.*227:151–159 (1957).

*Primary Examiner*—Robert A. Wax
*Assistant Examiner*—Dian C. Jacobson
*Attorney, Agent, or Firm*—Cushman Darby & Cushman, L.L.P.

[57] ABSTRACT

The present invention relates, in general, to an enzyme that degrades oxalic acid. In particular, the invention relates to the enzyme oxalate decarboxylase and to a DNA sequence encoding same. The invention further relates to a recombinant molecule comprising the oxalate decarboxylase encoding sequence and to a host cell transformed therewith. In addition, the invention relates to a method of protecting a plant from the deleterious effects of oxalic acid and to a method of reducing the oxalic acid content of a plant.

5 Claims, 3 Drawing Sheets

OXALATE DECARBOXYLATE

This is a continuation of Application Ser. No. 08/985,695, filed on Nov. 30, 1992, now abandoned.

BACKGROUND OF THE INVENTION

1. Technical Field

The present invention relates, in general, to an enzyme that degrades oxalic acid. In particular, the invention relates to the enzyme oxalate decarboxylase and to a DNA sequence encoding same. The invention further relates to a recombinant molecule comprising the oxalate decarboxylase encoding sequence and to a host cell transformed therewith. In addition, the invention relates to a method of protecting a plant from the deleterious effects of oxalic acid and to a method of reducing the oxalic acid content of a plant.

2. Background Information

Much of the oxalate from animals, including humans, originates from the oxalate ingested with plant material. Some green leafy vegetables (e.g. *Amaranthus, spinach, rhubarb*) are rich sources of vitamins and minerals, but they contain oxalic acid as a nutritional stress factor. Such plants, when consumed in large amounts, become toxic to humans because oxalate chelates calcium, and precipitation of calcium oxalate in the kidney leads to hyperoxaluria and destruction of renal tissues (Decastro, *J. Pharm. Biomed. Anal.* 6:1 (1988); Hodgkinson, *Clin. Chem.* 16:547 (1970)). Apart from this, at least two other instances can be cited where oxalic acid is involved in an indirect manner. In one case, the production of oxalic acid is an important attacking mechanism utilized by *Whetziinia sclerotiorium*, a fungus that causes serious damage to crops like sunflower. Oxalic acid accumulates in the infected tissues early in pathogenesis, and its concentration increases during the time the pathogen is colonizing the host tissues. The accumulation of oxalic acid in leaves causes symptoms of wilting and eventually leaf death. Thus, oxalic acid functions as a mobile toxin that moves from the base of stems of xylem sap and leaves (Maxwell, Physiol. Plant Pathol. 3:279 (1973)).

In another case, consumption of Lathyrus sativus (chickling vetch) causes neurolathyrism, which is characterized by spasticity of leg muscles, lower limb paralysis, convulsions, and death. *L. sativus* is a protein-rich hardy legume that grows under extreme conditions such as draught and waterlogging and does not require complex management practices. The neurotoxin β-N-oxalyl-L-α,β-diaminopropionic acid (ODAP) is present in various parts of the plant. ODAP synthesis is a two-step reaction in which oxalic acid is an essential starting substrate. ODAP acts as a metabolic antagonist of glutamic acid which is involved in transmission of nerve impulses in the brain. Hence, despite its rich protein content, the legume cannot be used as a food source (Mickelson et al, (1973) in Modern Nutrition in Health and Disease: Dietotherapy (Goodhart, R. S. and Shils, M. E., Eds) 5th Ed. pp. 412–433, Lea and Febiger, Philadelphia).

A study of the function of oxalic acid in the abovementioned systems highlights its role as an important stress factor. The value of an isolated gene encoding a protein product that degrades oxalic acid is clear. Such a gene could be used as a tool to effect degradation of oxalic acid in plants where it accumulates as such or is a substrate in the synthesis of neutoxin or is a medium for pathogenesis. This could be achieved by effecting single gene transfer to these plants.

Of the known oxalic acid-degrading enzyme systems, oxalate decarboxylase from the basidiomycetous fungus *Collybia velutipes* is of particular interest because of a report using partially purified enzyme that showed a simple single step breakdown of oxalic acid to carbon dioxide and formic acid, a nontoxic organic acid, in the absence of any cofactor requirement (Shimazono et al, J. Biol. Chem. 227:151 (1957)). The present invention provides purified oxalate decarboxylase and a DNA sequence encoding same. The invention also provides methods of using the encoding sequence to produce transgenic plants with low oxalic acid content. In so doing, the present invention makes possible the alleviation of stress conditions generated by oxalic acid in the cases mentioned above. It also makes possible the development of assay systems for monitoring urinary and serum oxalate levels.

OBJECTS AND SUMMARY OF THE INVENTION

It is an object of the invention to fully purify and properly characterize an oxalate decarboxylase.

It is another object of the invention to isolate, characterize and construct a gene that can be used in the expression of oxalate decarboxylase in microbes and in plants.

It is a further object of this invention to introduce an oxalate decarboxylase expressing gene into plants (including field crops such as sunflower, soybean, beans in general, rape/canola, alfalfa, flax, safflower, peanut and clover, vegetable crops such as lettuce, tomato, cucur bits, potato, carrot, radish, pea, lentils, cabbage, broccoli and brussel sprouts, flowers such as petunia and pyrethrum and tree species such as peach) thereby conferring on such plants resistance to diseases, especially fungal diseases, in which oxalic acid plays a major role, such as in diseases of the fungal genera *Sclerotinia, Sclerotium, Aspergillus, Streptomyces, Penicillium, Pythium, Paxillus, Mycena, Leucostoma, Rhizoctonia* and *Schizophyllum*.

The present invention is broadly directed to the use of an oxalate degrading enzyme, as exemplified by oxalate decarboxylase, for commercial uses such as in the brewing industry or for agronomic uses such as to reduce susceptibility of a plant to oxalic acid or to reduce the endogenous oxalic acid concentration in a plant. The oxalate degrading enzyme oxalate decarboxylase can be used to reduce plant mortality or destruction from diseases or other phenomenon in which oxalic acid plays a critical invasive role. Oxalate decarboxylase production can result in the prevention of plant mortality and infection from diseases in which oxalic acid is critical. Such diseases are particularly caused by, among others, the specific genera of fungi noted above.

Set forth herein is the invention of oxalate decarboxylase substantially purified and characterized. The enzyme has an acidic pI, is stable over a wide pH range and is moderately thermostable. The molecular weight of the enzyme, on SDS-PAGE, is 64 kDa in the glycosylated state and 55 kDa in the deglycosylated state.

Also set forth herein is the invention of substantially all of a substantially pure gene encoding an oxalate decarboxylase enzyme with a specific DNA sequence as shown in SEQ ID NO:1. The gene encodes an enzyme exhibiting oxalate decarboxylase activity having a molecular weight (degylcosylated) of approximately 55 kDa, as determined by SDS-PAGE.

The invention also relates to compositions for use in combatting plant patiogenesis, which compositions include chemicals exhibiting oxalic acid degrading activity, in particular oxalate decarboxylase activity. Specifically, the compound has oxalate decarboxylase activity in an amount sufficient to break down oxalic acid produced by pathogens. It will be appreciated that another agronomic use for such a compound is to combine the compound with an appropriate carrier, which is agronomically acceptable, permitting delivery of the compound directly to the plant or to the soil.

A transformed plant cell is also disclosed herein, which cell is transformed with a gene encoding oxalate decarboxylase. The gene encoding such an enzyme can include the DNA sequence set forth in SEQ ID NO:1.

A method is disclosed herein for providing protection against oxalic acid to a plant in need of such protection. The method includes providing, to a plant in need of such protection, an oxalic acid degrading enzyme in an amount sufficient to effect such protection. Preferably, it is envisioned that the oxalic acid degrading enzyme is oxalate decarboxylase encoded by a gene having the sequence set forth in SEQ ID NO:1. The methodology for providing such protection can take a plurality of forms including the transformation of a plant with a gene encoding an oxalic acid degrading enzyme and, in particular, encoding oxalate decarboxylase. Alternatively, the method can include provision of an oxalic acid degrading enzyme in combination with an agronomically acceptable carrier for direct application to a plant or to soil in which the plant grows.

Further objects and advantages of the present invention will be clear from the description of the invention that follows.

DETAILED DESCRIPTION OF THE INVENTION

Figure 1:
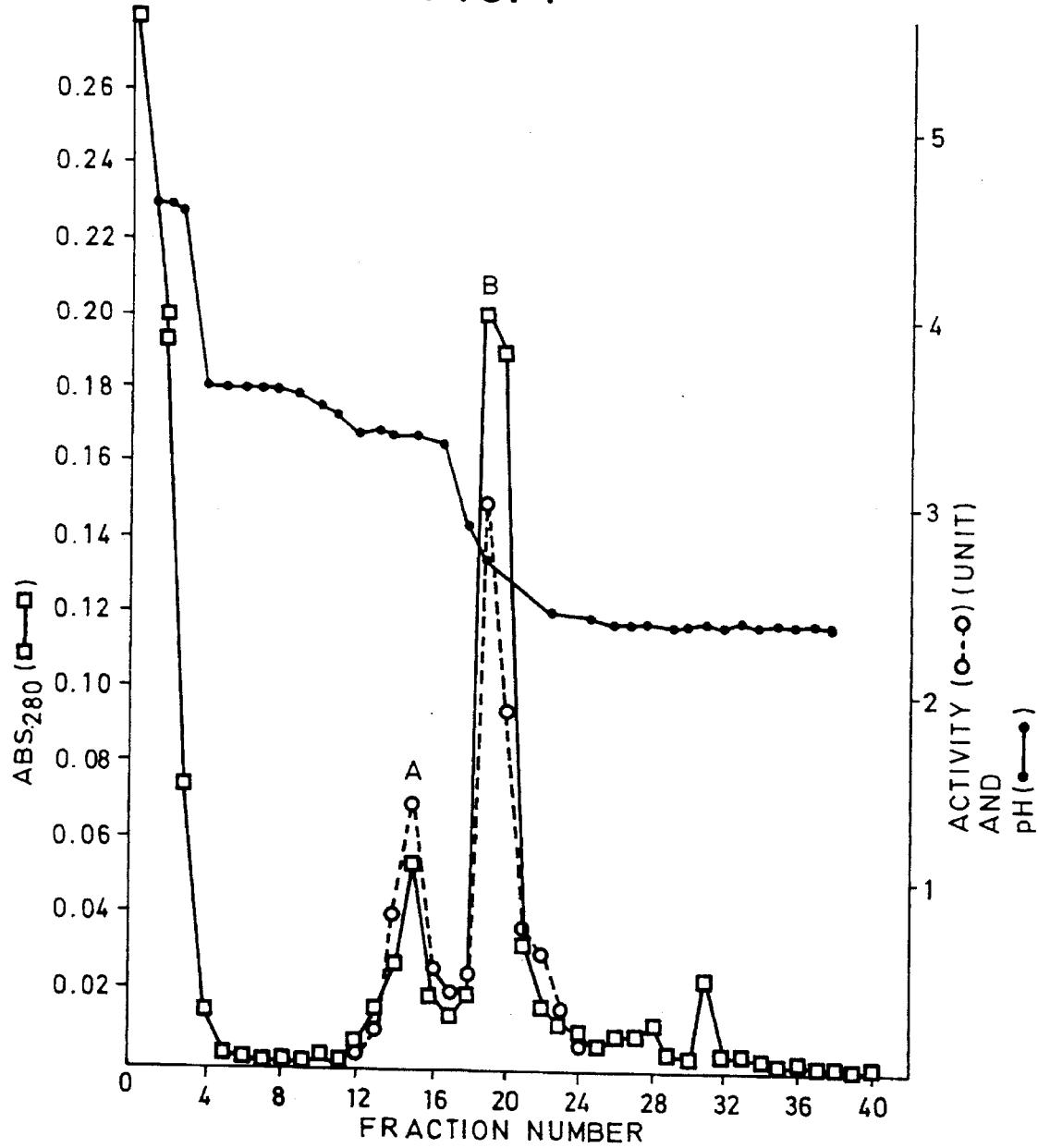
FIG. 1—Elution profile of oxalate decarboxylase from chromatofocusing column. The protein from the Acetone-IV step was loaded onto a DEAE-Sepharose CL-6B column (1×13 cm) equilibrated with 0.02M potassium acetate (pH 4.5). Bound proteins were eluted with a decreasing pH gradient. The activity was associated with peak A eluting at pH 3.3 and with peak B eluting at pH 2.5. Inset, protein bands corresponding to the two peaks. Peaks A (lane A) and (lane B) were resolved by 11% SDS-PAGE and stained with Coomassie Blue. Lane S shows molecular mass markers from Sigma (SDS-7).

The purified oxalate decarboxylase of this invention, its use as an agent to fight pathogenesis and its use in plant cell transformation provides a method of controlling plant diseases in which oxalic acid plays a critical role, either during pathogenesis or at the invasive stage. This invention holds special promise because a major scourge in the commercial cultivation of agronomically important plants, for example crops such as sunflowers, is caused by fungal species such as *Sclerotinia* that secrete oxalic acid.

The benefits of the present invention can be exploited either by plant transformation or by application of oxalate decarboxylase as a traditional pesticide most probably in combination with a suitable carrier that is agriculturally acceptable. One of the important benefits of the use of oxalate decarboxylase as a pesticide is that it is ecologically sound, non-polluting and does not harm the plant.

If an external application of the enzyme is to be used to protect a plant or plant part against pathogens, the enzyme can be diluted to form a liquid solution or suspension or mixed with diluent solid to be applied as a dust. The precise nature of application will depend in part on the particular pathogen(s) and plant(s) targeted. Detailed methods for adapting general methods of application to specific crops and pathogens can be found in "Methods for evaluating pesticides for control of plant pathogens". K. D. Hickey, ed., The American Phytopathological Society, 1986. Adjuncts that can be added to the formulation include agents to aid solubilization, wetting agents and stabilizers, or agents that produce a microencapsulated product. Such adjuncts are well-known in the art.

External applications can also utilize recombinant microorganisms in either a viable form or after being converted into a non-viable form by a method that does not inactivate the enzyme.

The purification of oxalate decarboxylase from *C. velutipes* is described in the Examples below, as is the characterization of the isolated enzyme. Two forms of the enzyme were resolved on chromatofocusing. The two isozymes were shown to be related by amino acid composition, peptide mapping, and immunological cross-reactivity. Peak A, eluting at pH 3.3, was used for further study; the $K_m$ was found to be 4.5 mM, and the $V_{max}$ was 166 μmol/min/mg. The subunit molecular mass of the glycosylated enzyme is 64 kDa, whereas the mass of the deglycoslated protein is 55 kDa. The enzyme shows an acidic pI, is very stable over a wide pH range, and is moderately thermostable.

The gene encoding the fungus-derived oxalate decarboxylase having the sequence shown in SEQ ID NO:1 was cloned as described in the Examples that follow. Briefly, the cDNA encoding the enzyme was obtained by immunoscreening a λgt11 expression library. In vitro translation of hybrid-selected mRNA gave a 55-kDa protein. Genomic Southern hybridization indicated that oxalate decarboxylase is encoded by a single gene. The cDNA probe hybridized to a single 1.5-kilobase pair species of mRNA. The mRNA was shown to be induced by oxalic acid. A temporal relationship between enzyme activity and mRNA levels was observed, indicating that the expression of oxalate decarboxylase is regulated at the transcription level.

The gene having the structure of SEQ ID NO:1 containing the coding sequence for the mature oxalate decarboxylase enzyme can be attached to genetic regulatory elements that are needed for the expression of the structural gene in a defined host cell. The first type of regulatory element required is a gene promoter region, which contains DNA sequences recognized by the biological machinery of the plant cell and which induces transcription of the DNA sequence into messenger RNA (mRNA). The mRNA is then translated into the protein product coded for by the structural gene region. The promoter is attached in front of or 5' to the gene for oxalate decarboxylase, which can be performed according to standard methods known in the art. See, for example, Maniatis et al, (1982) Molecular Cloning, Cold Spring Harbor Laboratory, New York, pp. 104–106.

Promoter regions which can be used for expression of the oxalate decarboxylase gene in plant cells include promoters which are active in a wide range of different plant tissues. For example, the 35S promoter from the cauliflower mosaic virus may be suitable for this purpose. Another type of promoter that can be used in plant cells is one that expresses under more restricted conditions. Included in this class are promoters active only in certain tissue(s) of the plant and/or induced to be active by certain stimuli like wounding. An example of this kind of promoter is the 5' regulatory region from the gene for phenylalanine ammonia lyase (PAL). This type of promoter is discussed in Liang et al, (1989), PNAS, U.S.A., 86:9284–9288. Expression of the oxalate decarboxylase gene in microbial hosts can be achieved by use of promoters obtained from microbial sources. Examples of such promoters include the trp promoter for expression in bacteria such as *E. coli*, as exemplified in Amann et al, (1983) Gene 25:167–178, or the glyceraldehyde phosphate dehydrogenase (GAPD) promoter for expression in yeast, as exemplified in Edens et al, (1984), Cell 37:629–633. The gene promoter sequences can also be derived in part or in whole from promoter sequences found in cells unlike those of the host cell as long as they meet the above criteria for transcription and translation.

A second genetic regulatory element which desirably can be, but need not be, attached to the oxalate decarboxylase gene is a terminator or polyadenylation sequence that promotes effective termination of transcription of the gene and, in eukaryotes, also promotes polyadenylation, i.e., the addition of any number of adenosine nucleotides at the 3' end of the mRNA. Standard methods known in the art can be used to attach the terminator region behind or 3' to the gene. (See, for example, T. Maniatis et al, supra, pp. 104–106). An example of such a terminator/polyadenylation sequence for expression in plants is that from the octopine synthase gene from an *Agrobacterium tumefaciens* Ti plasmid as enunciated in DeGreve et al, (1982), J. Mol. Appl. Genet. 1:499–511. An example of such a terminator for expression in microbial hosts is the rho-independent transcription terminator sequence from *Salmonella typhimurium*. See, for example, M. E. Winkler, (1987), "Escherichia coli and Salmonella typhimurium: Cellular and Molecular Biology", F. C. Neidhardt, ed.-in-chief; American Society for Microbiology. The gene terminator sequences can also be derived in part or in whole from terminator sequences found in cells unlike those of the host cell, as long as they meet the above criteria for transcription termination and polyadenylation required by the host cell.

Another type of regulatory element which can be attached to the gene for oxalate decarboxylase is a DNA sequence coding for a signal peptide. The signal peptide is attached to the amino terminus of the protein and permits the protein to be localized to the cell wall or secreted from the host cell. During this localization process, the signal peptide is cleaved off, producing a protein product with the sequence of the mature protein. The DNA sequence for the signal peptide is inserted between the promoter and the coding region. Standard methods known in the art may be used to attach the DNA sequence for the signal peptide (See, for example, Maniatis, T., et al., supra, pp. 104–106). Examples of such signal sequences include the signal peptide from an extensin gene of plants (Chen and Varner, 1985, EMBO J. 4:2145–2151) from the bacterial pelB (pectate lyase) gene of *Erwinia carotovora* (Lei et al, (1987), *J. Bacteriol.* 169:4379) and from prepro factor of yeast (Smith et al, 1985, Science 229:1219–1229). The signal peptide sequences can also be derived in whole or in part from signal sequences found in cells unlike those of the host cell, as long as they meet the above criteria for processing and localization of the protein in the host cell.

Any of the various methods known for introducing foreign genes into plants can be used for insertion of the oxalate decarboxylase gene into a host plant. The methodology chosen to accomplish plant transformation with the oxalate decarboxylase gene varies depending on the host plant. By way of example, one well-characterized methodology that would be useful for plant transformation with the oxalate decarboxylase gene is *Agrobacterium* mediated transformation.

*Agrobacterium* mediated transformation using the oxalic decarboxylase gene follows the procedures well-known for this methodology. First, a gene cassette suitable for expression in plants is introduced into a disarmed strain of *Agrobacterium tumefaciens* as in intermediate host. The oxalate decarboxylase gene cassette is introduced into the T-DNA region of a recombinant plasmid containing a selectable marker gene such as a gene encoding for neomycin phosphotransferase II, phosphinothricin acetyl transferease, or the like. This methodology is set forth in many literature publications including Horsch et al, (1985), Science 227:1229–1231. Pieces of plant tissue, e.g. leaf, cotyledon or hypocotyl are co-incubated with the bacteria for 2–3 days before the bacteria are killed using antibiotics such as carbenicillin. Additional antibiotics corresponding to the selectable marker gene employed are included in the plant tissue culture medium such that only transformed plant cells will grow.

Plants regenerated from the transformed cells are then tested for the presence and expression of the oxalate decarboxylase gene. Immunoassays and tests for oxalate decarboxylase activity can be used to identity individual transformants. Tolerance to exogenous oxalic acid can also be used as a functional test of intact tissues.

As noted, several other methodologies are available for plant transformation apart from *Agrobacterium* transformation. Examples of these other DNA delivery methods include electroporation, i.e. chemically induced delivery into protoplasts, micro-injection, biolistics, as well as others. An example of a types of plants that are not especially suitable for *Agrobacterium*-mediated transformation are soybean and certain cereals including maize. These plants would plainly benefit from plant transformation attempts using methodologies other than *Agrobacterium*-mediated transformation.

Certain aspects of the present invention will be described in greater detail in the non-limiting Examples that follow.

EXAMPLE 1

PURIFICATION AND CHARACTERIZATION OF OXALATE DECARBOXYLASE

Experimental Protocols

Organism and growth conditions:

*C. velutipes* (strain S. A.T.C.C 13547) was grown on the surface of medium containing 5% dextrose, 1% peptone, 0.1% $KH_2PO_4$, 0.05% $MgSO_4.7H_2O$) and 1% Difco malt extract at pH 5.2. The organism was grown from mycelial inoculation at 25° C. in stationary cultures in a volume of medium one-fifth the volume of culture flasks. About 25 days after inoculation, the enzyme oxalate decarboxylase was induced by addition of 12.5 mM oxalic acid to each culture flask. The mycelium was harvested 2 to 3 days after the addition of oxalic acid and the mycelial pad was washed with cold distilled water and stored at −20° C. *C. velutipes* was maintained on slants of the same medium (Jakoby, Methods in Enzymology 5:637 (1962)).

Purification:

Step 1. Preparation of crude extract. The frozen mycelium was ground in a Waring blender for 10 min with either dry ice or liquid nitrogen. The powder was extracted with three volumes of 0.1M potassium citrate buffer, pH 3.0 for 10 min a 4° C. and the suspension centrifuged at 10,000×g for 30 min at 4° C. The supernant was filtered through a double layer of cheese cloth.

Step 2. Precipitation with acetone. The acetone concentrations were adopted from Shimazono and Hayaishi (J. Biol. Chem. 227:151 (1957)) except that the last two steps were not performed. The percentages quoted are on vol/vol basis assuming additive volumes. (a) Low temperature for acetone precipitation was maintained by an ice-salt bath at −10° C. The sample was chilled to 0° C. and the first acetone precipitation at 33.3% was given by dropwise addition of chilled acetone to supernatant with constant mechanical stirring (Acetone-I). The mixture was equilibrated for 15 min and the precipitate formed was removed by centrifugation in a precooled rotor at 10,000×g, 20 min at 2° C. The precipitate obtained from 33.33%–50% fractionation was dissolved in one-fifth the starting volume of cold 0.1M potassium acetate buffer at pH 4.5. The enzyme solution was dialyzed for 16 hours, 4° C. against two changes of 0.02M potassium acetate buffer, pH 4.5, and a small precipitate formed during dialysis was removed by centrifugation (Acetone-II). (b) Supernatant was brought to 40% acetone (Acetone-III) and the precipitate obtained was discarded. The precipitate from further addition to 50% (Acetone-IV) was dissolved in a small volume of 0.02M potassium acetate, pH 4.5.

Step 3. Chromatofocusing. DEAE-Sepharose CL-6B (Pharmacia) was equilibrated in 0.02 M potassium acetate buffer, pH 4.5, and used to pack a 10 ml column (1×13 cms bed). The precipitate from the last acetone precipitation was loaded at a flow rate of 10 ml/h. The column was washed with two column volumes of 0.02M potassium acetate, pH 4.5, and the elution effected by developing an internal pH gradient using 4 mM acidic buffer mix (4 mM each of DL-aspartic acid, L-glutamic acid and glycine, pH 2.3). The elation was done at a flow rate of 10 ml/h and 2 ml fractions collected; proteins were monitored by absorbance at 280 nm; the fractions were assayed for enzyme activity and the pH of each fraction determined. The fractions containing enzyme activity were pooled and dialyzed against water and concentrated in Amicon microconcentrator (30,000 cut off). The enzyme was stored at 4° C.

Enzyme assay:

The oxalate decarboxylase activity was also determined by measuring the liberation of $^{14}CO_2$ from [$^{14}C$]-oxalic acid (Amersham, 4.1 mCi/mmol). The enzyme assay was carried out in small glass vails which contained 1 ml of the following reaction mixture: 0.2M potassium citrate, pH 3.0, 0.005M potassium oxalate, pH 3.0, 5.6 nmoles (0.0227 µCi) of ($^{14}C$)-oxalic acid and 0.2 ml of enzyme solution. The tubes were preincubated for 5 min before the addition of enzyme. The tubes were sealed with rubber-stoppers and incubated at 37° C. for 30 min in a shaking water bath. The reaction was terminated by injection of 0.2 ml of 50% v/v trichloroacetic acid through the rubber caps and the tubes were shaken for additional 60 min to trap all the $^{14}CO_2$ evolved in the 0.2 ml methylbenzethonium hydroxide(Sigma) placed in a plastic vial inside the glass tube. The plastic wells were withdrawn and the contents transferred to 5 ml of toluene based scintillation fluid and radioactivity determined in a liquid scintillation counter. Blanks tubes were set up in which the 0.2 ml of 50% TCA was added before the enzyme or the enzyme was omitted. In kinetic experiments, the values were corrected for the radioactivity obtained from the boiled denatured enzyme.

Definition of a unit:

One unit was defined as the amount of enzyme releasing 1 µmole of $^{14}CO_2$ per min at 37° C. under standard assay conditions. The overall assay efficiency was usually between 60–70%. Protein was determined by Lowry microassay method (Peterson, Anal. Biochem. 83:346 (1977)). $V_{max}$ and $K_m$ were determined by Lineweaver-Burk plot (Lineweaver and Burk, J. Am. Chem. Soc. 56:658–666 (1934)).

Molecular mass determination:

The molecular mass of oxalate decarboxylase was determined by gel filtration chromatography. Purified enzyme (100 µg in 100 µl) was loaded on a FPLC gel permeation column (Superose 12: 10×300 nm) at a flow rate of 0.5 ml/min using 0.02M potassium acetate buffer, 0.1M KCl, pH 4.5, at room temperature. Proteins were detected at 280 nm. Standard proteins used were thryoglobulin (660 kDa, Pharmacia), ferritin (440 kDa, Pharmacia) catalase (230 kDa, Pharmacia), aldolase (158 kDa, Pharmacia), alcohol dehydrogenase (150 kDa, Sigma) and carbonic anhydrase (29 kDa, Sigma). The subunit composition was determined by sodium dodecyl sulfate polyacrylamide slab gel electrophoresis in 7% to 15% gradient gels using Laemmli buffer system (Laemmli, Nature 227:680 (1970)).

Criteria of purity:

Homogeneity of purified oxalate decarboxylase was determined by resolving 10 µg of protein (peak A) on two-dimensional gel electrophoresis according to O'Farrell (O'Farrell, J. Biol. Chem. 250:4007 (1975)).

Amino acid composition:

Samples were hydrolized in 6M HCl in evacuated and sealed tubes at 110° C. for 22 hr. The hydrolysates were analyzed with an amino acid analyzer (LKB 4151 Alpha Plus). Cysteine and cystine were determined as cysteic acid after performic acid oxidation. Tryptophan was not determined. Digestion with VB protease was done as described earlier, (Cleveland, Methods in Enzymol. 96:222) (1983)).

Carbohydrate analysis:

Glycoprotein staining was done by using the Periodate-Schiff base reagent. The natural sugar content was determined by phenol-sulfuric acid method (McKelvy et al, Arch. Biochem. Biophys. 132:99 (1969)) with glucose as standard. The enzyme was deglycosylated by Endo-β, N-acetyleglucosaminidase H from *S. plicatus*, (Boehringer Manneheim, 40 mU/µg) according to Trimble (Trimble et al, Anal, Biochem. 141:515 (1984)).

Preparation of antiserum:

The oxalate decarboxylase (1 mg/ml) was heat denatured by boiling for 10 min in PBS in presence of 0.5% SDS. The protein antigen (150 µg) in PBS was emulsified with Freund's complete adjuvant and injected subcutaneously in a New Zealand White rabbit. Subsequent boosters were given in Freund's incomplete adjuvant subcutaneously after a period of three weeks. Fourth injection was given intravenously. Antibody titer was monitored using Ouchterlony immunodiffusion technique (Garvey et al (1977) Methods in Immunol, 3rd Ed, W. A. Benjamin Inc., N.Y.). The affinity purfication of antibody was done according to Iwaki et al (Iwaki et al, Cell 57:71 (1989)).

Western blotting and immunodetection:

Proteins were transferred to a nitrocellulose membrane (Schleicher & Schuell) at 150 mA constant current for 3 hour at 15° C. according to the procedure of Towbin et al (Proc. Natl. Acad. Sci. U.S.A. 76:4350 (1979)). Immunodetection was done using 1:5000 dilution of anti-oxalate decarboxylase antibody and detected via alkaline phosphatase reaction (Amersham, Super-screen immunoscreening system).

Figure 2:
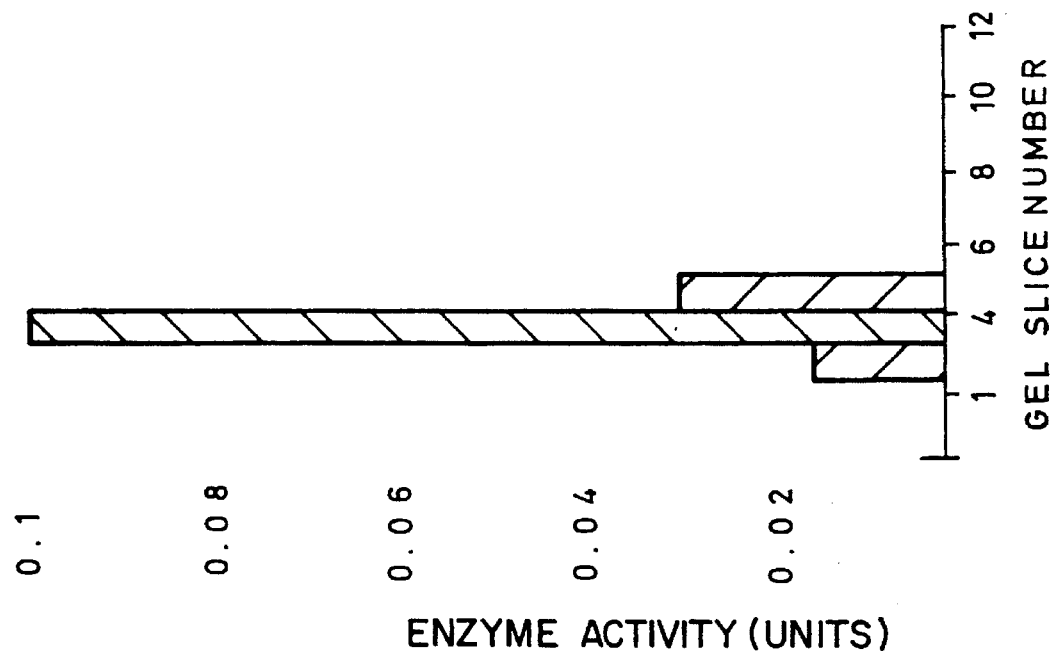
FIG. 2—Activity-band correlation. 500 ng protein was electrophoresed in two lanes of 6% non-denaturing polyacrylamide gel; one lane was stained with Coomassie blue and the other was cut into twelve 4 mm sections. The gel slices were incubated in 200 μl of 0.1M potassium acetate buffer, pH 4.5. The acrylamide was mashed and soaked overnight at 4° C. Enzyme activity was assayed and correlated to the band in stained lane. The migration distance ($R_f$ of 0.35, gel slice no. 4) of enzyme activity (0.2 units) correlated with that of the single stained band (500 ng). No protein band or enzyme activity was found in any other part of the gel.

Results:

Maximal activity of oxalate decarboxylase was obtained 2 or 3 days after the addition of oxalic acid. The results of a typical purification procedure are given in Table 1. The enzyme resolved into two peaks on a chromatofocusing column: peak A eluted at pH 3.3, and peak B eluted at pH 2.5 (FIG. 1). Peak A was purified 1670-fold with 2.9% recovery, whereas peak B coeluted with two minor contaminants and was purified 614-fold with 15% recovery (Table 1). These contaminants could be removed after passage through a Sepharose 4B gel filtration chromatography column, and this protein was used for determining amino acid composition. Because of the high purity of peak A, this protein was used for further work. The material in peak A eluted as a single peak on a fast protein liquid chromatography Superose 12 column, and 10 μg of protein gave a single spot on two-dimensional gel electrophoresis. The serial 2-fold dilutions of the enzyme showed that at least 45 mg of protein can be detected by Coomassie Blue staining. The migration distance of enzyme activity ($R_f$=0.35, gel slice 4) correlated with that of the single stained band on nondenaturing PAGE (FIG. 2). No protein bands or enzyme activity was found in any other part of the gel. Thus, the protein band corresponding to peak A had the oxalate decarboxylase activity. Enzyme preparations were stable at 4 or −20° C., and >70% of the initial activity could be measured after 4 months of storage at 4° C. at 1 mg/ml in 0.02M potassium acetate (pH 4.5).

TABLE 1

PURIFICATION TABLE FROM A TYPICAL EXPERIMENT[a]

| Purification Step | Total Protein (mg) | Total Activity (Units) | Specific Activity (Units/mg) | Purification Fold | Yield % |
|---|---|---|---|---|---|
| 1. Crude extract | 4480 | 950 | 0.21 | 1 | 100 |
| 2. Acetone II | 120 | 608 | 5.06 | 24 | 64 |
| 3. Acetone IV | 3.8 | 260 | 68.8 | 328 | 27.3 |
| 4. Chromato focusing | | | | | |
| a. Peak A | 0.08 | 28 | 350 | 1670 | 2.9 |
| b. Peak B | 1.24 | 160 | 129 | 614 | 16.8 |

[a]150 g of liquid nitrogen ground powder used.

Amino acid composition data of the two peaks indicated the presence of a very high content of acidic amino acids (22%) (Table 2). This could account for their low pI values, although the proportion amidated in native protein was not determined. The two peaks had very similar amino acid compositions, except for a 2-fold higher methionine and tyrosine content in peak B and a 2-fold higher cysteic acid content in peak A. Further relatedness was indicated by the peptide map of the two peaks using *Staphylococcus aureus* V8 protease. The affinity-purified antibodies directed against peak A cross-reacted with peak B protein. The amino acid composition, peptide maps, and immunological cross-reactivity indicate that the two peaks resolved on chromatofocusing are related to each other. The two forms with differences in pI may arise from different degrees of amidation or acidic amino acids or may be due to microheterogeneity in the constituent oligosaccharide chains.

TABLE 2

AMINO ACID COMPOSITION

| | Peak A %[a] | Peak B % |
|---|---|---|
| Asx | 10.57 | 10.31 |
| Glx | 11.75 | 11.52 |
| Lys | 3.2 | 2.96 |
| Arg | 2.84 | 2.89 |
| His | 2.66 | 2.74 |
| Gly | 8.44 | 9.44 |
| Ser | 7.23 | 7.19 |
| Thr | 8.56 | 8.48 |
| Cys[c] | 0.66 | 0.28 |
| Tyr | 0.84 | 1.85 |
| Ala | 11.03 | 10.92 |
| Val | 6.31 | 6.52 |
| Leu | 7.79 | 7.19 |
| Ile | 4.00 | 3.86 |
| Pro | 8.64 | 8.46 |
| Phe | 5.13 | 4.68 |
| Met | 0.34 | 0.69 |
| Trp | ND[b] | ND |
| Ammonia | ND | ND |

[a]Mole percent
[b]Not determined
[c]Determined as cystic acid

The molecular mass of the native enzyme estimated by gel filtration was 560 kDa. Electrophoresis on 7–15% gradient SDS-polyacrylamide gel showed the presence of a single polypeptide of 64 kDa. This molecular size was consistently obtained with all different gel percentages used with the Laemmli bufffer system. When the enzyme was treated with endo-β-N-acetylglucosaminidase H, the size of the major deglycosylated band was 55 kDa. The enzyme was found to be glycosylated, and the high apparent molecular size obtained by gel filtration could be due to the tendency of certain glycoproteins to interact noncovalently in solution (Farach—Carson et al, Biotechniques 7:482 (1989); Kleinman et al, Biochemistry 25:312 (1986)).

From Lineweaver-Burk plots, an apparent Km, value of 4.5 mM was calculated for potassium oxalate as the substrate. This gave a $V_{max}$ of 166 μmol/min/mg. The enzyme was competitively inhibited by phosphate ions, and a Ki of 9 mM was obtained when 90 mM $PO_4^{2-}$ was added to the reaction. The enzyme was specific for oxalate as the substrate since citric acid, acetic acid, oxalacetic acid, succinic acid and formic acid were not used as substrates.

The enzyme was not irreversibly inactivated over a wide range of pH values, and the pH optimum for decarboxylation is 3.0 The enzyme retained 78% of the initial activity after 20 minutes of incubation at 80° C. Almost total inactivation occurred at 96° C. within 10 minutes of incubation. Enzyme activity was unaffected by sulfhydryl group reagents as the enzyme retained 95% of its activity in the presence of 50 mM p-chloromercuribenzenesulfonic acid or 50 mM iodoacetate. Oxalate decarboxylase retained 45% of its activity after incubation with 10% SDS for 30 minutes at room temperature. However, when heated to 60° C. in the presence of 10% SDS, almost all of the activity was lost. The glycoprotein nature of the protein was indicated by positive staining with periodate-Schiff base reagent; it bound to concanavalin A-Sepharose and was eluted with 0.5M α-methylmannoside. The neutral sugar content was estimated to be 15% by the phenol/sulfuric acid method.

Figure 3:
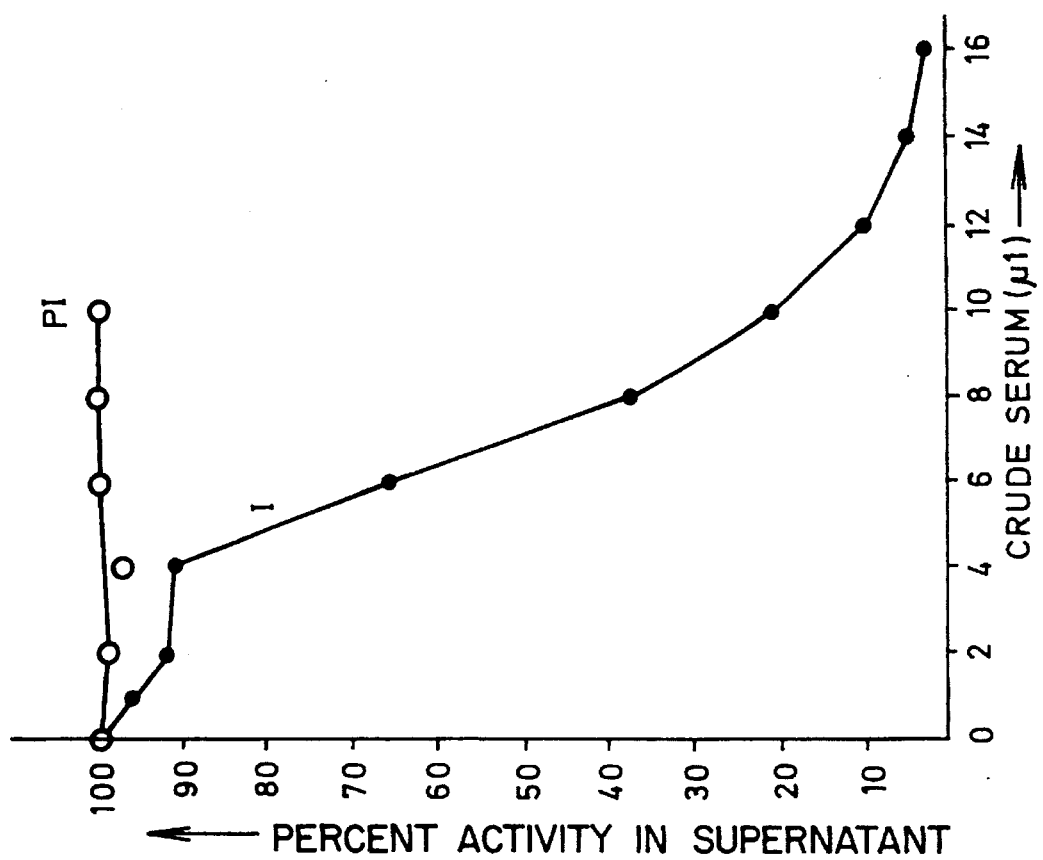
FIG. 3—Immunotitration of enzyme activity. 1.5 μg of enzyme in 0.02M potassium acetate buffer, pH 4.5, was incubated with different volumes of serum (1) at 25° C. for 2 hours. Immunocomplexes were spun down at 12,000×g for 10 min and residual activity determined by standard assay. Control incubation was carried out with preimmune serum (P1).

Immunotitration of the enzyme with 8 µl of crude antioxalate decarboxylase antiserum brought down >60% of the initial activity in the supernatant (FIG. 3). The antiserum against oxalate decarboxylase used at a dilution of 1:5000 could detect a minimum of 1.0 ng of peak A protein. The antiserum cross-reacted with all the peptides obtained from V8 protease digests and with the deglycosylated forms of peaks A and B of the enzyme. The antiserum that was affinity-purified against peak A protein cross-reacted with peak B of oxalate decarboxylase and oxalyl-CoA decarboxylase from Oxalobacter formigenes strain OxB. It did not cross-react with oxalate oxidase from Hordeum vulgare (barley).

EXAMPLE 2

MOLECULAR CLONING AND EXPRESSION OF DNA ENCODING OXALATE DECARBOXYLASE

Experimental Protocol

Molecular cloning:

Total RNA was extracted from liquid nitrogen ground powder of *C. velutipes* according to the method of Chomczynski and Sacchi (Anal. Biochem. 162:156 (1987)) and poly(A+) RNA was selected by two cycles of chromatography on oligo (dT) cellulose. cDNA synthesis and cloning and immunoscreening of the library were performed following the instructions of Amersham. The cDNA was synthesized from mRNA of 12 hours oxalate induced culture by oligo(dT) priming of 5 µg of poly (A+) RNA and cloned into the EcoRI restriction site of lambda gt11. The packaged phages were grown in *E. coli* host Y1090 r- for immunoscreening. Antioxalate decarboxylase antibodies were preadsorbed with 1 mg/ml *E. coli* Y1090 cell lysate to remove background reactivity and used for immunoscreening. Goat anti-rabbit IgG alkaline phosphatase conjugate was used for detection of positive clones. The DNA was prepared from immunopositive phages according to Del Sal (Biotechniques 7:514 (2989)) and their insert size determined. Fusion proteins were characterized according to (Anal. Biochem. 156:354 (1986)); relatedness of inserts was studied by using one of inserts as probe. The 1.2 kb insert from clone number 3 was subcloned in pTZ18U (USB) and used as a probe for other experiments.

Differential hybridization:

Differential hybridization of immunopositive clones was studied by preparing single-stranded cDNA probes synthesized from mRNA isolated from mycellum at 0 hour and 12 hour of induction by oxalate. Recombinant phage DNA (0.5 µg) was bound to Gene Screen Plus membrane in duplicate Hybri-slot™ Filtration manifold according to the instructions in Gene Screen Plus manual and hybridized to oxalate induced and uninduced cDNA probes. The specific activity of the probe was $2 \times 10^8$ cpm/µg cDNA.

Hybridization:

Hybridization of DNA and RNA blots was at 42° C. using the formamide procedure in Gene Screen Plus manual. An overnight prehybridization was done in 50% deionized formamide, 1% SDS, 1M sodium chloride, 10% dextran sulfate. The blots were hybridized to denatured probe (1–4× $10^5$ dpm/ml) at 42° C. for 24 hour. The membranes were washed successively in 2 washes each of 2×SSC at room temperature, 2×SSC plus 1% SDS at 65° C. for 30 min, 0.1×SSC at room temperature for 30 min. Damp membranes in plastic wraps were exposed to Kodak XAR films in present of intensifying screen.

Probe preparation:

The subcloned DNA in pTZ18U was digested with EcoRI and resolved on 2% low melting agarose gel insert DNA was incised and labeled with ($\alpha$-$^{32}$P)dATP by the random primer labelling method of Feinberg and Vogelstein (Anal. Biochem. 137:226 (1984)).

Genomic DNA Isolation and Southern analysis:

Genomic DNA was isolated from lyophilized *C. velutipes* by the method of Zolan and Pukkila (Mol. Cell. Biol. 6:195 (1986)). The DNA was banded twice on CeCl gradient to obtain DNA that could be digested with restriction enzyme. Four micrograms of genomic DNA was digested with various restriction endonucleases and resolved on 1.2% agarose gel. The DNA was transferred to Gene Screen Plus membrane by alkaline blotting procedure (Reed and Mann, Nucleic Acids Res. 13:7207 (1985)).

In vitro translation:

Poly(A+) RNA was translated using a rabbit reticulocyte lysate according to manufacturer's instructions (Promega). The translated proteins were precipitated by specific antisera and analyzed by SDS-polyacrylamide gel electrophoresis.

Hybrid selection:

Hybrid selection of oxalate decarboxylase mRNA was performed by hybridizing poly(A+) RNA (20 µg in 200 µl 65% formamide, 10 mM PIPES, pH 6.4, 0.4M NaCl, 8 mM EDTA, 0.5% SDS, 100 µg/ml yeast tRNA) at 50° C. 4 hour, to Gene Screen Plus membrane on which denatured cDNA (4 µg) had been bound. Filters were prepared according to Gene Screen Plus manual and hybridization, washing and elution of hybridized RNA was performed (Jagus, Methods in Enzymol. 152:567 (1987); Parnes et al, Proc. Natl. Acad. Sci. U.S.A 78:2253 (1981)). The eluted RNA was extracted with phenol:chloroform (1:1), precipitated in ethanol, reconstituted directly in in vitro translation mix and immunoprecipitated according to Anderson and Blobel (Methods in Enzymology 96:111 (1983)).

Northern blot analysis:

One µg of poly (A+) RNA or 10 µg of total RNA was denatured with glyoxal and resolved on 1.2% agarose gels according to Sambrook (Sambrook et al (1989) Molecular Cloning: A Laboratory Manual, Cold Spring Harbor Laboratory, Cold Spring Harbor, N.Y.) and capillary blotted onto the Gene Screen Plus membrane as instructed in Gene Screen Plus manual. Filters were probed with $^{32}$P-labeled 1.2 kb cDNA insert.

Results:

As noted above, a cDNA expression library was constructed from 12-h oxalate-induced mRNA in λgt11. Approximately 47,000 recombinants were screened with the antibody pretreated with *E. coli* lysate. Fifteen immunopositive plaques were obtained and plaque-purified; of these 12 cross-hybridized. These encoded fusion proteins of sizes comparable to insert sizes. The phage DNA from 15 immunopositive clones was immobilized onto a Gene Screen Plus membrane in duplicate and probed with oxalate-induced and uninduced cDNA probes. Differential hybridization of the 15 immunopositve clones showed that 12 hybridized to the cDNA probe from oxalate plus mRNA and gave no signal with oxalate minus mRNA. Thus, the expression of 12 clones was induced by oxalate.

The pTZ18U subclone of the 1.2-kb insert from λ clone 3 was used to hybrid-select the mRNA. The in vitro translation of hybrid-selected RNA and immunoprecipitation of the translated product gave a band of 55 kDA, which was similar to the size obtained with total poly(A+) mRNA and corresponded to the size of the deglycosylated protein. This 55-kDa protein was not obtained when mRNA was omitted (FIG. 8B, lane 1) or with the nonrecombinant vector sequences. The 55-kDa product was obtained with 12-h mRNA and not with uninduced 0-h mRNA; the 55-kDa band was shown to be related to oxalate decarboxylase as the purified oxalate decarboxylase competed for antigen-binding sites and caused a decrease in the intensity of the 55-kDa band in the in vitro translation and immunoprecipitation experiments.

Genomic Southern blots using the 1.2-kb insert as probe showed the presence of single bands with the BamHI EcoRI, HindIII, PvuII, SspI, XbaI, and XhoI digests, indicating the presence of a single copy gene. The two bands of unequal intensities obtained with KpnI and PstI were due to the presence of internal sites (single site for each enzyme) in the 1.2-kb cDNA insert for these enzymes. The 1.2-kb probe hybridized to a single species of mRNA of 1.5 kb from 12-h oxalate-induced poly(A+) RNA, and no hybridization to RNA from the uninduced lane was seen.

Figure 4:
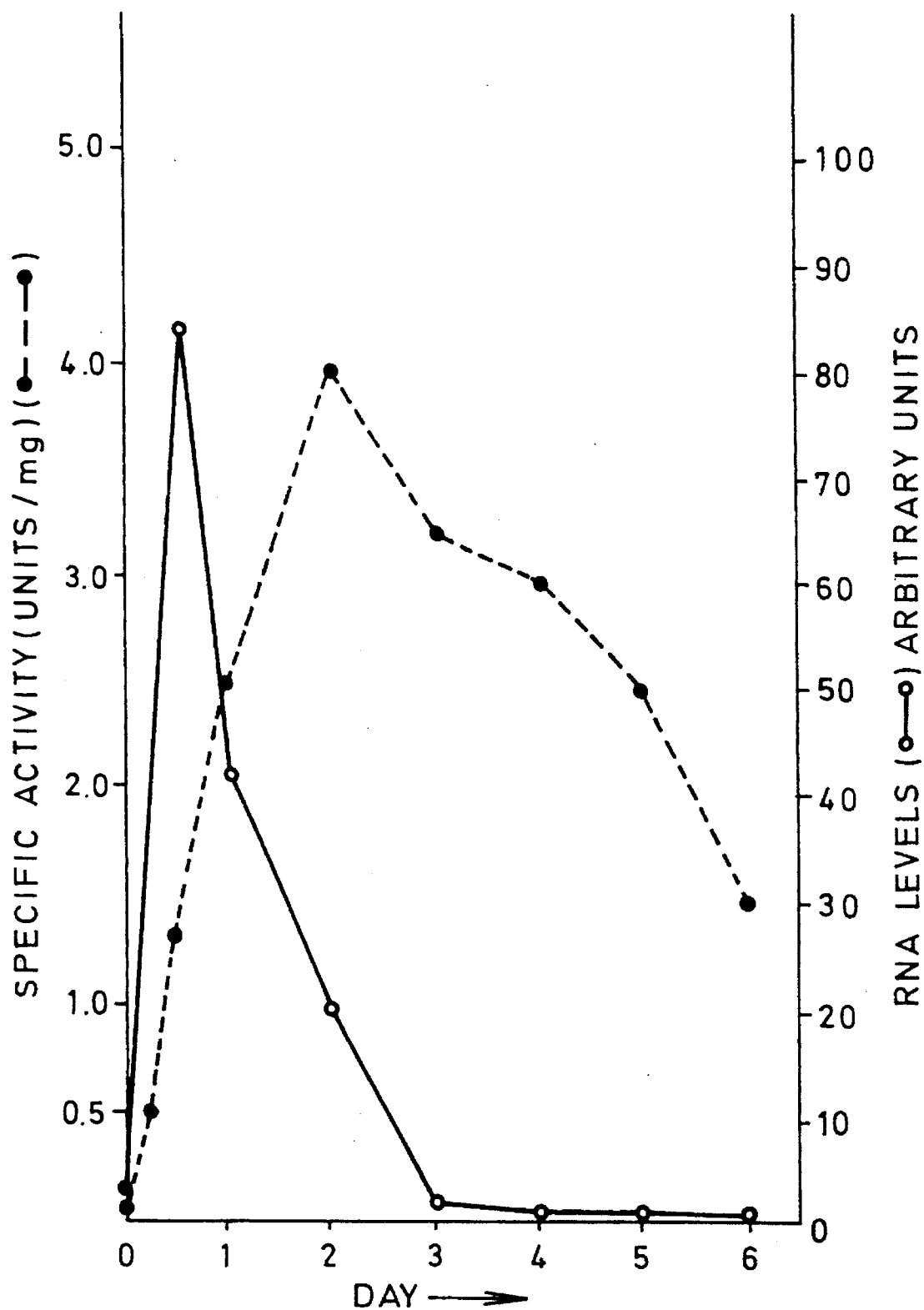

From the same batch of cultures, samples were collected from different stages after induction and were analyzed for RNA levels, enzyme activity, and total protein. The Northern blot of total RNA showed that the 1.5-Kb band was absent at 0 h and peaked at 12 h. No RNA could be detected 3 days after induction. Enzyme activity was detected 12 h after the addition of oxalate and peak activity was seen on day 2, after which there was a steady decline. An associated increase or decreases in total protein was not observed (FIG. 4). Hence, a temporal relationship was observed between the appearance of enzyme activity and the mRNA levels since the mRNA levels peaked 12 h after induction and the maximal enzyme activity was obtained 48 h after the addition of oxalic acid.

All references cited hereinabove are incorporated by reference.

One skilled in the art will appreciate from a reading of this disclosure that various changes in form and detail can be made without departing from the true scope of the invention.

SEQUENCE LISTING ( 1 ) GENERAL INFORMATION:

( i i i ) NUMBER OF SEQUENCES: 1

( 2. ) INFORMATION FOR SEQ ID NO:1:

( . i ) SEQUENCE CHARACTERISTICS:
( A ) LENGTH: 1445 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:1:

```
ATCGCATTCC GATGTTCAAC AACTTCCAAC GTCTGCTCAC TGTCATCCTT CTCTCCGGTT      60
TTACCGCTGG AGTGCCTTTG GCGTCCACCA CGACGGGAAC TGGAACTGCG ACCGGTACCT     120
CAACCGCCGC AGAGCCCAGC GCGACTGTCC CCTTCGCCAG CACTGATCCC AACCCCGTGC     180
TCTGGAATGA GACCAGTGAC CCAGCGCTTG TAAAGCCAGA GAGGAACCAG CTTGGTGCGA     240
CAATCCAAGG ACCGGATAAT CTGCCTATAG ACCTTCAGAA TCCGGACTTG CTCGCCCCAC     300
CGACTACTGA TCATGGCTTT GTCGGTAATG CGAAGTGGCC ATTCAGCTTC AGCAAGCAGC     360
GACTGCAGAC GGGTGGCTGG GCTCGGCAGC AGAATGAGGT CGTTTTGCCT CTCGCGACTA     420
ATCTCGCTTG CACAAATATG CGTCTTGAAG CAGGCGCTAT CAGGGAGCTG CATTGGCACA     480
AGAACGCTGA GTGGGCATAT GTTCTGAAGG GGTCTACCCA AATCTCAGCT GTCGATAACG     540
AAGGGCGCAA TTATATTTCC ACCGTCGGCC CTGGTGATTT GTGGTACTTC CCACCAGGCA     600
TTCCTCACTC GCTACAAGCG ACAGCCGATG ATCCAGAAGG CTCAGAGTTC ATCTTAGTCT     660
TTGATTCAGG CGCCTTCAAT GACGACGGTA CATTCTTGCT CACTGACTGG CTTTCGCATG     720
TTCCAATGGA AGTTATCCTG AAGAACTTCA GAGCCAAGAA TCCCGCCGCA TGGTCTCACA     780
TACCTGCTCA ACAGCTATAC ATCTTCCCTA GTGAACCTCC TGCGGACAAC CAGCCGGACC     840
CCGTTAGCCC ACAGGGGACG GTTCCCCTTC CATATTCATT CAACTTCTCC TCTGTCGAGC     900
CGACGCAGTA TTCCGGTGGG ACAGCGAAGA TTGCAGATTC CACGACGTTC AACATTTCCG     960
```

| | | | | | | |
|---|---|---|---|---|---|---|
| TCGCTATCGC | CGTGGCCGAG | GTTACAGTTG | AGCCTGGTGC | TTTGAGAGAG | CTGCACTGGC | 1020 |
| ATCCGACTGA | GGACGAGTGG | ACATTCTTCA | TCTCTGGAAA | CGCGAGGGTG | ACAATTTTCG | 1080 |
| CTGCGCAGAG | TGTAGCCTCT | ACGTTTGATT | ACCAAGGTGG | TGATATCGCT | TATGTTCCTG | 1140 |
| CATCTATGGG | CCATTATGTA | GAGAACATTG | GAAACACGAC | TTTGACTTAT | CTGGAGGTCT | 1200 |
| TCAATACCGA | CCGTTTTGCT | GATGTCAGTC | TAAGTCAGTG | GCTGGCGTTA | ACACCTCCGA | 1260 |
| GTGTCGTGCA | GGCGCACCTG | AACTTGGACG | ACGAGACACT | TGCGGAGCTC | AAGCAGTTTG | 1320 |
| CGACCAAGGC | GACTGTTGTT | GGTCCTGTGA | ACTGAACTTT | CGTTCCTTTA | AACTCATCAA | 1380 |
| ATTATCATTG | GAATTCTATG | TAGATGTTGT | AATCAATGCA | GTTCTTCGGC | TAAAAAAAA | 1440 |
| AAAAA | | | | | | 1445 |

What is claimed is:

1. An isolated and purified DNA fragment encoding oxalate decarboxylase, having the sequence of SEQ ID No. 1.

2. The fragment according to claim 1 wherein said fragment encodes fungal oxalate decarboxylase.

3. The fragment according to claim 2 wherein said fragment encodes *Collybia velutipes* oxalate decarboxylase.

4. A recombinant molecule comprising the DNA fragment of claim 1 and a vector.

5. A transformed plant cell comprising the molecule according to claim 4.

* * * * *